(12) United States Patent
Hughes

(10) Patent No.: US 8,231,846 B2
(45) Date of Patent: Jul. 31, 2012

(54) IDENTIFICATION TAG WITH PERFORATIONS FOR A LABORATORY SAMPLE CASSETTE

(75) Inventor: Thomas Fergus Hughes, Eastbourne (GB)

(73) Assignee: Raymond A Lamb Limited, Eastbourne, East Sussex (GB)

( * ) Notice: Subject to any disclaimer, the term of this patent is extended or adjusted under 35 U.S.C. 154(b) by 363 days.

(21) Appl. No.: 12/526,723

(22) PCT Filed: Feb. 14, 2008

(86) PCT No.: PCT/GB2008/050096
§ 371 (c)(1),
(2), (4) Date: Aug. 11, 2009

(87) PCT Pub. No.: WO2008/099216
PCT Pub. Date: Aug. 21, 2008

(65) Prior Publication Data
US 2010/0093071 A1    Apr. 15, 2010

(30) Foreign Application Priority Data
Feb. 14, 2007   (GB) .................................. 0702881.4

(51) Int. Cl.
| | |
|---|---|
| *B01L 3/00* | (2006.01) |
| *G01N 27/00* | (2006.01) |
| *H04Q 5/22* | (2006.01) |
| *G01N 21/75* | (2006.01) |
| *C12M 3/00* | (2006.01) |
| *G08B 1/08* | (2006.01) |
| *G02B 21/34* | (2006.01) |

(52) U.S. Cl. ..................... 422/554; 422/82.01; 422/500; 422/503; 422/551; 422/518; 435/288.3; 435/288.4; 435/288.7; 435/6.11; 340/10.1; 340/539.12; 359/396

(58) Field of Classification Search ........................ None
See application file for complete search history.

(56) References Cited

U.S. PATENT DOCUMENTS
2002/0030598 A1 * 3/2002 Dombrowski et al. .... 340/572.1
(Continued)

FOREIGN PATENT DOCUMENTS
DE    101 12 899 A1    10/2002
(Continued)

OTHER PUBLICATIONS
International Search Report for PCT/GB2008/050096.

*Primary Examiner* — In Suk Bullock
*Assistant Examiner* — Jennifer Wecker
(74) *Attorney, Agent, or Firm* — Fay Sharpe LLP

(57) ABSTRACT

A tag (1) for a laboratory sample cassette has a first layer (3). A chip (8) is mounted on a surface (7) of the first layer (3), and an antenna (6) is printed on the surface of the first layer (3). The antenna (6) is arranged to establish communication between the chip (8) and an electric or electronic read/write device. A second layer (4) is positioned and bonded against the surface (7) and has a hole (9) which passes through the second layer (4). The hole (9) contains the chip (8) and a third layer (5) covers the hole (9) from the opposite side to the first layer (3), the third layer (5) being bonded to the second layer (4). Thus, the antenna (6) and chip (8) are sealed within the tag (1). A plurality of perforations (10) are provided which pass through all the layers (3,4,5) of the tag (1) from one side of the tag (1) to an opposite side thereof to enable liquid to pass through the tag (1).

11 Claims, 4 Drawing Sheets

U.S. PATENT DOCUMENTS

| | | |
|---|---|---|
| 2002/0172016 A1 | 11/2002 | Reiner |
| 2006/0035247 A1 | 2/2006 | Ko et al. |
| 2006/0220789 A1* | 10/2006 | Suzuki et al. ................ 340/10.1 |
| 2006/0239867 A1 | 10/2006 | Schaeffer |
| 2007/0193021 A1* | 8/2007 | Kobayashi et al. ............. 29/601 |
| 2008/0055045 A1* | 3/2008 | Swan et al. .................. 340/10.1 |

FOREIGN PATENT DOCUMENTS

| | | |
|---|---|---|
| DE | 10112899 A1 * | 10/2002 |
| DE | 10 2005 927 441 A1 | 12/2006 |
| GB | 2 379 739 A | 3/2003 |
| GB | 2379739 A * | 3/2003 |

* cited by examiner

IDENTIFICATION TAG WITH PERFORATIONS FOR A LABORATORY SAMPLE CASSETTE

This application is the national filing of and claims the benefit of International Patent Application No. PCT/GB 2008/050096, filed on Feb. 14, 2008 and claims the priority benefit of GB Patent Application Serial No. 0702881.4, filed Feb. 14, 2007, the subject matter of which is incorporated herein by reference.

The present invention relates to a tag for a cassette for laboratory samples.

A laboratory tissue sample may be processed by being placed in a laboratory sample cassette which is in the form of a tray and a lid is then placed on top of the tray. The cassette and sample is then passed through a tissue processor where chemical liquids pass through holes in the cassette. On leaving the tissue processor the sample is removed from the cassette and placed in a mould where it is orientated and the mould is filled with wax or resin. A glass bead containing an electronic tag is then inserted into the wax. The cassette is then placed on top of the mould so that the cassette becomes bonded to the wax or resin block as it sets. The sample in the wax or resin on the cassette can then be sent to be processed such as by being cut by a microtome.

A problem with using the tag in the above process is that the tag can only be used to keep track of the sample from when the tag is inserted into the wax. Another problem is that it is difficult for an electric or electronic read/write device to read the tag as it is not known exactly where the tag is within the wax and the tag is difficult to read as its aerial is small. Also, linked to the difficulty of reading the tag there is a problem in that the read/write device always needs to be placed facing the wax on the cassette so that it is close as possible to the tag.

It is an object of the present invention to alleviate the aforementioned problems.

The invention consists in a tag for a laboratory sample cassette, comprising a first layer, a micromodule having a memory medium for storing information and being on a surface of the first layer, an antenna on said surface of the first layer, said antenna arranged to establish communication between the micromodule and an electric or electronic read/write device, a second layer positioned against said surface and having a recess which contains the micromodule, the antenna and micromodule being sealed within the tag, and at least one perforation passing through all the layers of the tag from one side of the tag to an opposite side thereof to enable liquid to pass through the tag.

By having the antenna and micromodule sealed in the tag, they are protected from chemicals used in the tissue processor, enabling the tag to be with the sample from the time the sample is placed in the cassette. By providing the antenna on the surface of the first layer it can be spread over a significant area thus facilitating read/write communication with the micromodule. By having at least one perforation passing through all the layers of the tag from one side of the tag to an opposite side thereof enabling liquid to pass through the tag, this makes it easier for the tag to be used in the tissue processor as chemicals can pass through the tag perforation(s).

In one embodiment the recess is a hole that passes through the second layer. A third layer may cover the hole from the opposite side to the first layer.

In another embodiment the recess in the second layer is a blind hole that contains the micromodule.

Each layer of the tag is preferably bonded to the adjacent layer or layers.

The tag may comprise a radio frequency identification (RFID) tag. This provides a greater read range enabling much greater flexibility in the positioning of the electric or electronic read/write device for reading the tag. The tag enables an ultrahigh frequency (UHF) antenna to be part of it.

The tag may include fixing means for attaching the tag to the laboratory sample cassette.

There may be provided a laboratory sample cassette including a tag as previously described. The fixing means may engage at least one complementary perforation or hole in the cassette to hold the tag to the cassette. At least one said perforation of the tag may be sufficiently aligned with a perforation or hole in the cassette to enable liquid to pass through the sufficiently aligned perforations.

The micromodule has a memory medium for storing information. The micromodule may comprise a chip such as a RFID chip, which operates in a contactless mode. The chip comprises an integrated circuit having a memory of the kind which is re-writable, such as an electrically erasable programmable read-only memory (EEPROM), so that information in the memory can be written over or erased by new information which is subsequently written to the memory using the electronic read/write device.

Embodiments of the present invention will now be described, by way of example, with reference to the schematic accompany drawings, in which:—

Figure 1:
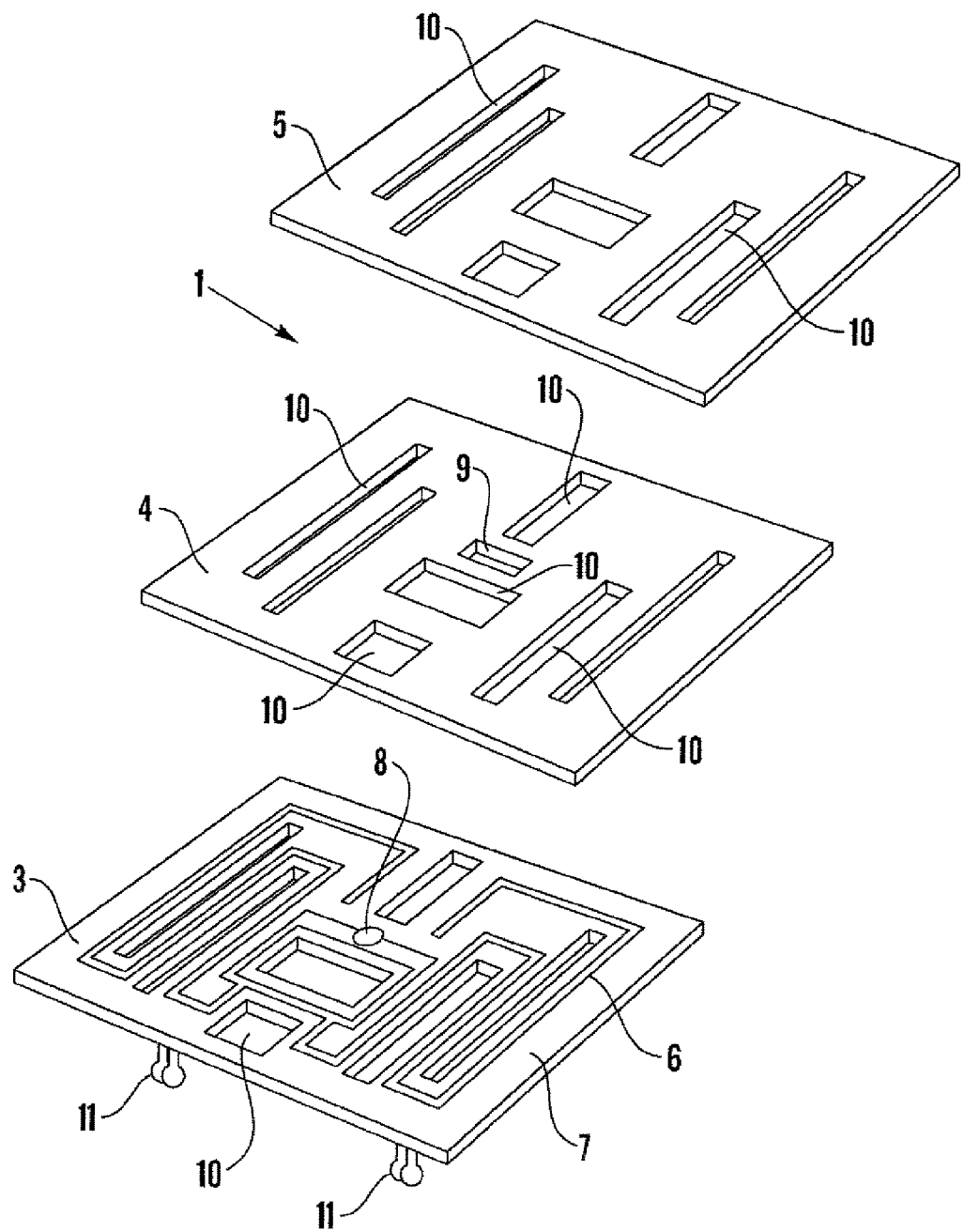
FIG. 1 is an exploded perspective view of a tag according to one embodiment of the present invention.
Figure 2:
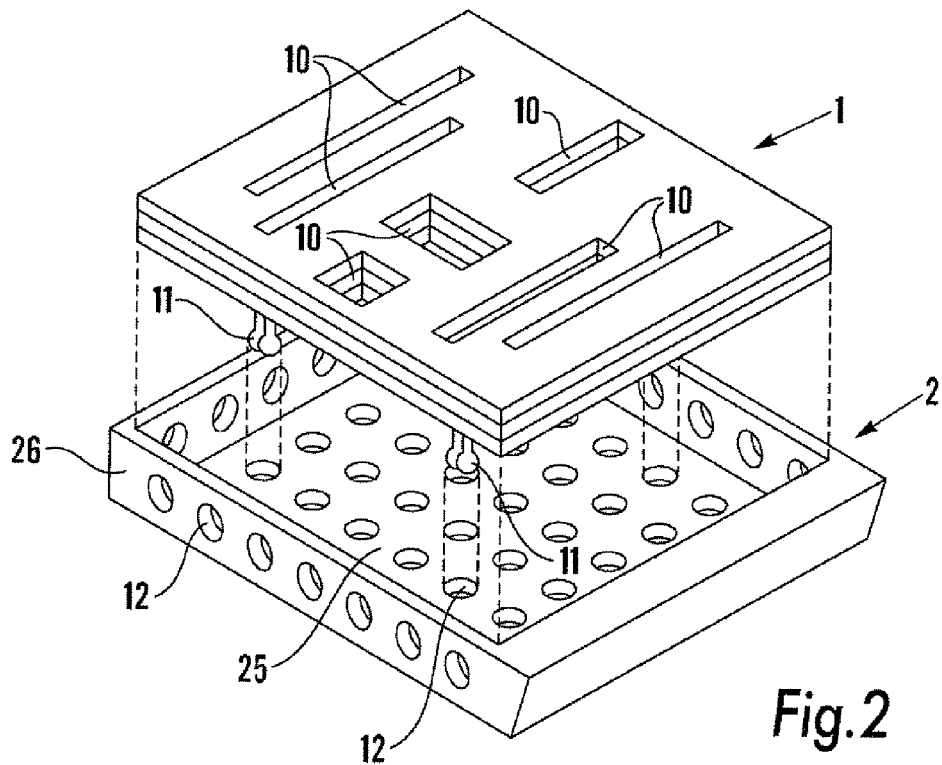
FIG. 2 is a perspective view of the tag and a laboratory sample cassette to which the tag is to be fixed.
Figure 3:
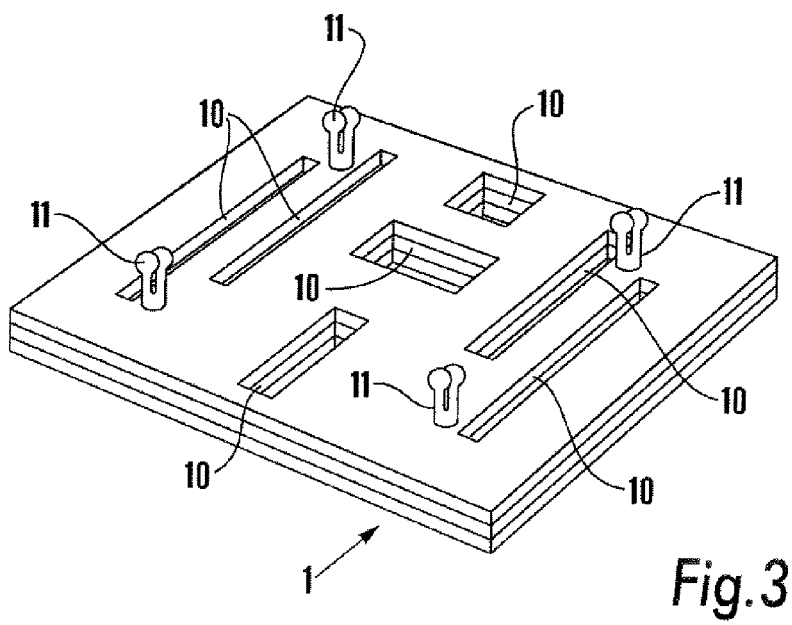
FIG. 3 is a perspective view of the underside of the tag.

Referring to FIGS. 1 to 3 of the accompanying drawings, a tag 1 for a cassette 2 for a laboratory sample, comprises a laminate having a first or base layer 3, a second or recessed layer 4 and a third or cover layer 5.

An antenna 6 is printed or otherwise deposited on a surface 7 of the base layer 3. A micromodule 8 is applied to the surface 7 using a surface mounting mechanism and is connected to the antenna 6. The micromodule 8 is in the form of an RFID chip which comprises an integrated circuit, and the antenna 6 serves as an interfacing means for electrically interfacing the integrated circuit to the circuit of a digital read/write device. The recessed layer 4 has a recess 9 in the form of a hole passing through the recessed layer 4. The recessed layer 4 is bonded to the base layer 3 so that the chip 8 is received in the hole 9. The cover layer 5 covers the hole 9 from the opposite side to the base layer 3 and is bonded to the recessed layer 4. The material for the layers 3,4,5 and bonding are resistant to chemicals used in processing the laboratory sample and the antenna 6 and chip 8 are sealed within the tag 1 and are accordingly protected from such chemicals.

Each layer 3,4,5 has a plurality of perforations 10 with at least some of the perforations varying in size. The perforations 10 are at least partially aligned to form holes passing from one side of the tag 1 to an opposite side thereof. Preferably, the perforations 10 are similarly dimensioned and positioned for all three layers 3,4,5 so that when the three layers 3,4,5 are connected together to form the laminate, the perforations 10 of the three layers 3,4,5 are all aligned.

The tag 1 has fixings or lugs 11 extending from the base of the tag 1 and these are arranged to engage with holes 12 in the laboratory sample cassette 2 to hold the tag 1 to the cassette 2. The holes 12 may be in a base portion 25 and/or side portions 26 of the cassette.

In use, the tag 1 is placed in a laboratory sample cassette 2 which is in the form of a tray. The tag 1 is of a size so that it just fits within the tray and the tag lugs 11 are inserted into holes 12 in the cassette 2. A tissue sample is then placed in the cassette 2 above the tag 1 and a lid with holes (not shown) is placed on top of the tray to create a secure chamber for the sample. The cassette 2 with the tag 1 and sample is then passed through a tissue processor where chemical liquids pass through the perforations 10 in the tag 1 and through the holes 12 in the cassette 2. The perforations 10 are sufficiently aligned with a number of holes 12 in the cassette to enable liquids to pass through. On leaving the tissue processor the sample is removed from the cassette 2 and placed in a mould (not shown) where it is orientated and the mould is filled with wax or resin. The cassette 2 is then placed on top of the mould so that the cassette 2 becomes bonded to the wax or resin block as it sets. The sample in the wax or resin on the cassette 2 can then be sent to be processed such as by being cut by a microtome.

Figure 4:
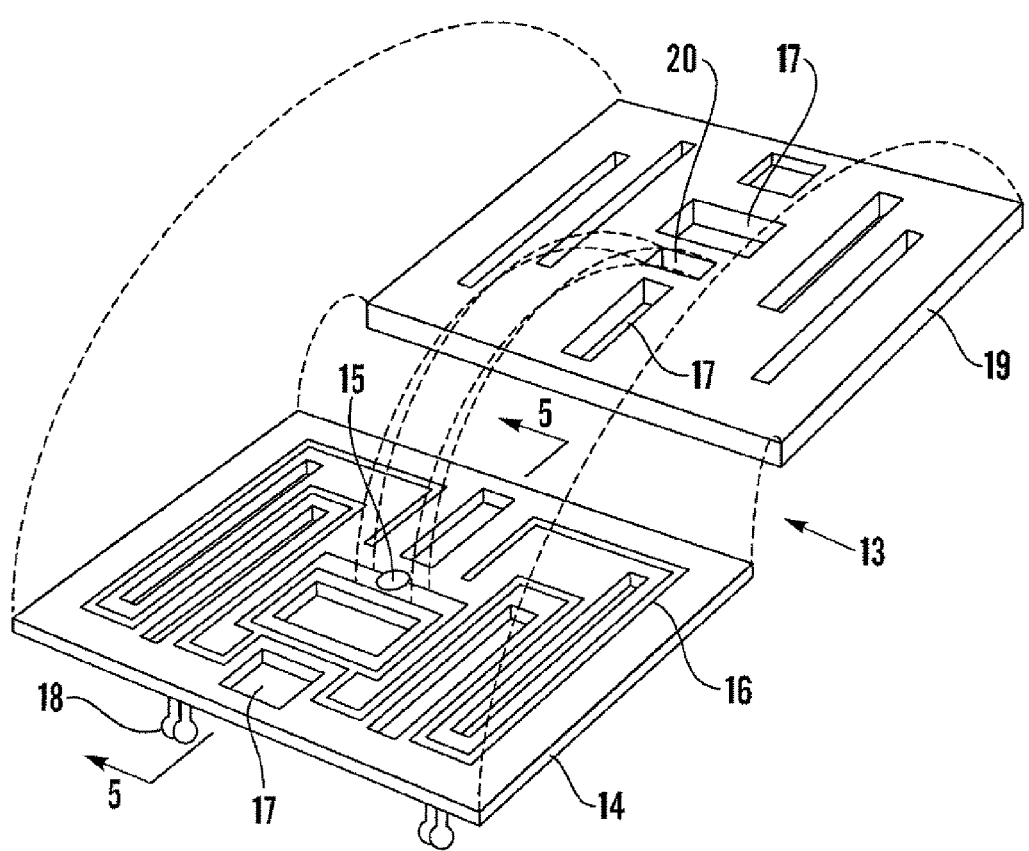
FIG. 4 is an exploded perspective view of a tag according to a second embodiment of the present invention.
Figure 5:
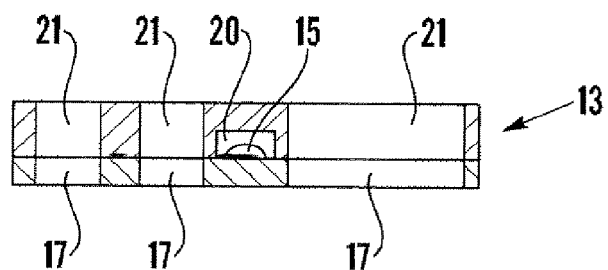
FIG. 5 is a cross-sectional view of the tag in its assembled state taken along lines 5-5 of FIG. 4.

Referring to FIGS. 4 and 5, an injection moulded tag 13 is shown having a base layer 14 with a chip 15, antenna 16, perforations 17 and lugs 18 as previously described and a recessed or second layer 19, wherein the recess 20 in the recessed layer 19 is a blind hole or indent that contains the chip 15. Thus, the recessed layer 19 covers and seals chip 15 when the recessed layer 19 is bonded to the base layer 14 and there is no need for the third layer. The recessed layer 19 also has perforations 21 to align with perforations 17 in the base layer 14 so that the tag 13 has holes passing from one side of the tag 13 to an opposite side thereof.

Figure 6:
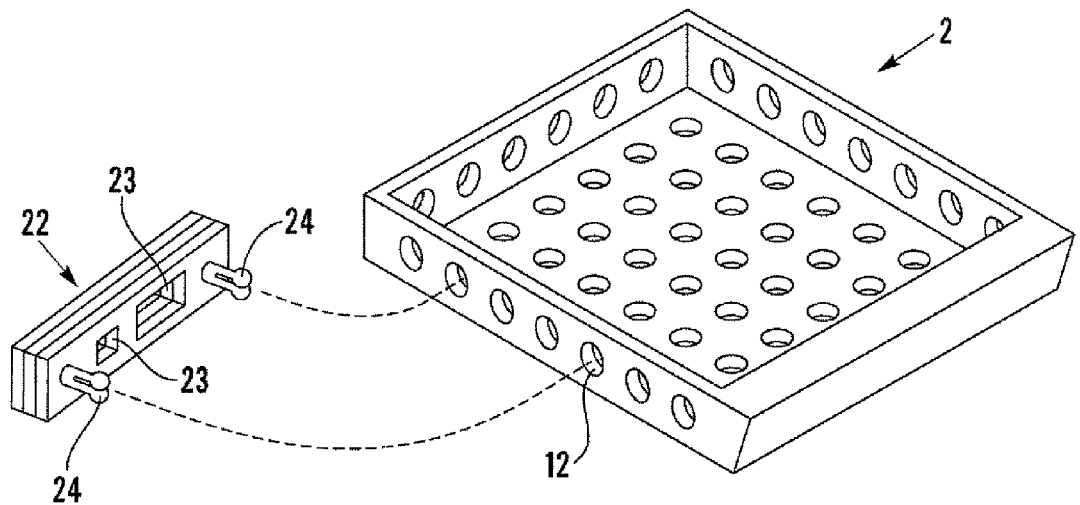
FIG. 6 is a perspective view of a tag according to a third embodiment of the present invention being attached to a side of a laboratory sample cassette.
Figure 7:
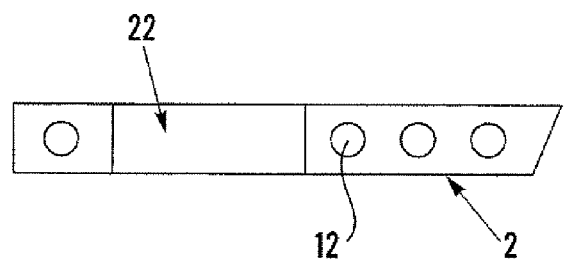
FIG. 7 is an elevational view of the tag of FIG. 6 attached to the side of the cassette.

Referring to FIGS. 6 and 7, another modified tag 22 with a different shape and different perforations 23 is shown. The tag 22 has lugs 24 placed on the base of the tag 22 to be inserted into holes 12 in a side of a laboratory sample cassette 2 so that the tag 22 is on the outside of the cassette 2.

Figure 8:
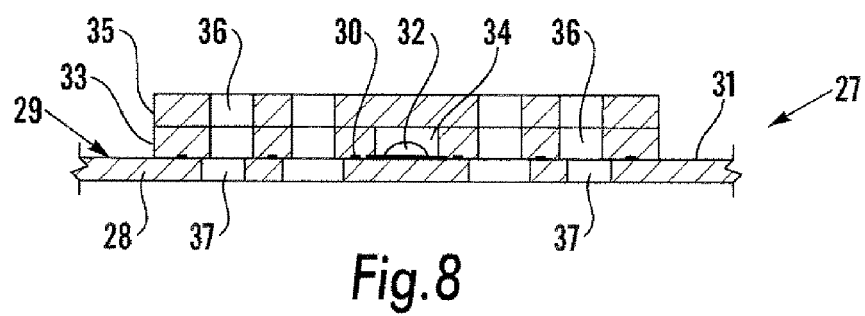
FIG. 8 is a cross-sectional view of a tag according to a fourth embodiment of the present invention.

Referring to FIG. 8, the base layer of the tag 27 has been replaced by the base portion 28 of the laboratory sample cassette 29. The antenna 30 is printed or otherwise deposited on a surface 31 of the base portion 28 and the chip 32 is applied to the surface 31 with both the antenna 30 and chip 32 avoiding holes 37 in the base portion 28 of the cassette 29. The recessed layer 33 is bonded to the base portion 28 so that the chip 32 is received in the hole 34 in the recessed layer 33. The cover layer 35 covers the hole 34 from the opposite side to the base portion 28 and is bonded to the recessed layer 33. Perforations 36 in the recessed layer 33 and cover layer 35 are sufficiently aligned with holes 37 in the base portion 28 of the cassette 29 to enable liquids to pass through. In a modification to this embodiment, the recessed and cover layers can be replaced by a recessed layer with a bind hole like the tag 13 illustrated in FIGS. 4 and 5.

Whilst particular embodiments have been described, it will be understood that various modifications may be made without departing from the scope of the invention. The tag may be of different sizes and have different number and sizes of holes passing through it. The tag may be used with different forms of laboratory sample cassettes and is not limited to tray shaped cassettes. The cassettes may not necessarily have perforations on their sides.

A laboratory sample cassette may be moulded with the tag.

The micromodule may comprise more than one integrated circuit and the recessed layer may have more than one hole or indent. The antenna may be a copper antenna applied by an electroplating process.

The invention claimed is:

1. A combination of a tag and a laboratory sample cassette, the tag comprising a first layer, a micromodule having a memory medium for storing information and being on a surface of the first layer, an antenna on said surface of the first layer, said antenna arranged to establish communication between the micromodule and an electric or electronic read/write device, a second layer positioned against said surface and having a recess which contains the micromodule, the antenna and micromodule being sealed within the tag, and at least one perforation passing through all the layers of the tag from one side of the tag to an opposite side thereof to enable liquid to pass through the tag from one side of the tag, and at least one fixing member engaging at least one complementary perforation in the cassette to hold the tag to the cassette.

2. The combination of the tag and laboratory sample cassette as claimed in claim 1, wherein the recess is a hole that passes through the second layer.

3. The combination of the tag and laboratory sample cassette as claimed in claim 2, wherein a third layer covers the hole from the opposite side to the first layer.

4. The combination of the tag and laboratory sample cassette as claimed in claim 1, wherein the recess in the second layer is a blind hole that contains the micromodule.

5. The combination of the tag and laboratory sample cassette as claimed in claim 1, wherein each layer is bonded to the adjacent layer or layers.

6. The combination of the tag and laboratory sample cassette as claimed in claim 1, wherein the micromodule is in the form of a radio frequency identification chip.

7. The combination of the tag and laboratory sample cassette as claimed in claim 1, wherein the antenna is a UHF antenna.

8. The combination of the tag and laboratory sample cassette as claimed in claim 1, wherein at least one said perforation of the tag is sufficiently aligned with a perforation in the cassette to enable liquid to pass through the sufficiently aligned perforations.

9. The combination of the tag and laboratory sample cassette as claimed in claim 1, wherein the cassette has a base portion and said base portion forms the first layer of the tag.

10. A laboratory sample cassette having an integral tag, the tag comprising a first layer, a micromodule having a memory medium for storing information and being on a surface of the first layer, an antenna on said surface of the first layer, said antenna arranged to establish communication between the micromodule and an electric or electronic read/write device, a second layer positioned against said surface and having a recess which contains the micromodule, the antenna and micromodule being sealed within the tag, and at least one perforation passing through all the layers of the tag from one side of the tag to an opposite side thereof to enable liquid to pass through the tag, wherein at least one said perforation of the tag is sufficiently aligned with a perforation in the cassette to enable liquid to pass through the sufficiently aligned perforations.

11. The laboratory sample cassette as claimed in claim 10, wherein the tag is moulded into the cassette.

* * * * *